US006472528B1

(12) United States Patent
Gross et al.

(10) Patent No.: US 6,472,528 B1
(45) Date of Patent: Oct. 29, 2002

(54) SYNTHESIS OF SUBSTITUTED PYRAZOLOPYRIMIDINES

(75) Inventors: Raymond S. Gross, San Diego, CA (US); Keith M. Wilcoxen, San Diego, CA (US); Richard Oglesby, Poway, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 0 days.

(21) Appl. No.: 09/636,727

(22) Filed: Aug. 9, 2000

Related U.S. Application Data

(60) Provisional application No. 60/148,313, filed on Aug. 10, 1999, and provisional application No. 60/148,314, filed on Aug. 10, 1999.

(51) Int. Cl.[7] .................... C07D 487/00; C07D 471/02; C07D 231/00
(52) U.S. Cl. ................. 544/281; 546/119; 546/121; 548/365.7
(58) Field of Search ............... 546/119, 121; 548/365.7; 544/281

(56) References Cited

U.S. PATENT DOCUMENTS

| 4,521,422 A | 6/1985 | Dusza et al. ............ 514/258 |
| 4,626,538 A | 12/1986 | Dusza et al. ............ 514/258 |
| 4,654,347 A | 3/1987 | Dusza et al. ............ 514/258 |
| 4,900,836 A | 2/1990 | Tomcufcik et al. ...... 546/279 |
| 5,538,977 A | 7/1996 | Dusza et al. ............ 514/258 |
| 6,060,478 A | * 5/2000 | Gilligan et al. ......... 514/258 |

FOREIGN PATENT DOCUMENTS

| WO | WO 99/57101 | 11/1999 |

OTHER PUBLICATIONS

Dusza et al., "The Synthesis of CL 285,489, N–Methyl–N–[3–[3–(–2–thienylcarbonyl)–pyraxolo[1,5–alyprimidin–7–yl]phenyl]acetamide, a Potent Sedative," Study Code 34060–003, Jul. 7, 1989.
Foster, "Developments in CNS Drugs II: Drugs of Tomorrow," SMi Conference, London, UK, May 11–12th, 1999.

* cited by examiner

Primary Examiner—Richard L. Raymond
Assistant Examiner—Tamthom N. Truong
(74) Attorney, Agent, or Firm—SEED Intellectual Property Law Group PLLC

(57) ABSTRACT

Methods of making substituted pyrazolopyrimidines generally and, more particularly, N-methyl-N-(3-{3-[2-thienylcarbonyl]-pyrazol-[1,5-α]pyrimidin-7-yl}phenyl)acetamide. Such compounds have utility over a wide range of indications, including treatment of insomnia. In the practice of the present invention, improved techniques which do not require use and/or isolation of the pyrazole intermediate are disclosed, as well as improved techniques for making the reaction intermediates themselves. Such techniques offer significant advantages, including enhanced efficiency, particularly in the context of large scale manufacture.

21 Claims, No Drawings

SYNTHESIS OF SUBSTITUTED PYRAZOLOPYRIMIDINES

CROSS-REFERENCE TO RELATED APPLICATIONS

This application claims the benefit of U.S. Provisional Application No. 60/148,313 filed Aug. 10, 1999 and Ser. No. 60/148,314 filed Aug. 10, 1999.

TECHNICAL FIELD

This invention is directed to the synthesis of substituted pyrazolopyrimidines, which compounds have utility over a wide range of indications including treatment of insomnia.

BACKGROUND OF THE INVENTION

U.S. Pat. No. 4,521,422 to American Cyanamid Company is directed to certain aryl and heteroaryl[7-(aryl and heteroaryl)-pyrazolo[1,5-a]pyrimidin-3-yl]methanones which are active as anxiolytic, anticonvulsant, sedative-hypnotic and skeletal muscle relaxant agents. Such compounds may generally be classified as "substituted pyrazolopyrimidines" having the following structure (I):

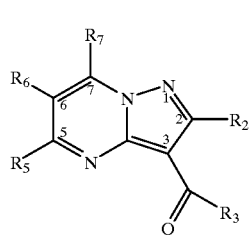

(I)

wherein $R_2$, $R_3$, $R_5$, $R_6$, and $R_7$ are as defined in U.S. Pat. No. 4,521,422 (but under a different numbering scheme for the various R groups).

Compounds of structure (I) are made according to U.S. Pat. No. 4,521,422 by reacting an appropriately substituted pyrazole (a) with an appropriately substituted 3-dimethylamino-2-propen-1-one (b) as represented by the following Reaction Scheme A Reaction Scheme A

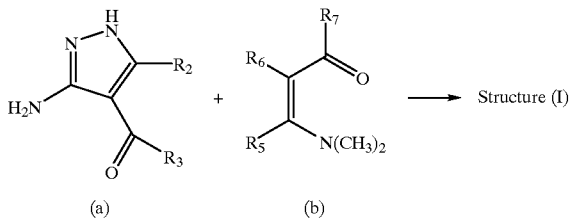

U.S. Pat. No. 4,900,836, also to American Cyanamid Company, discloses novel pyrazoles (a) for use in Reaction Scheme A. More specifically, in this patent pyrazoles (a) are made, as represented below in Reaction Scheme B, by reacting appropriately substituted acetonitrile (c) with a dimethylamide dimethyl acetal (d) to yield the corresponding propanenitrile (e), which is then reacted with aminoguanidine nitrile (f) to give the correspondingly substituted pyrazole (a).

Reaction Scheme B

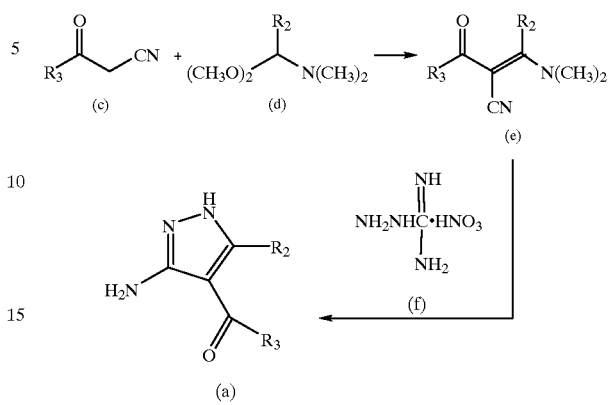

U.S. Pat. No. 4,521,422 also discloses the synthesis of substituted pyrazolopyrimidines of structure (I) using starting intermediates other than substituted 3-dimethylamino-2-propen-1-ones (b). For example, as represented by Reaction Scheme C, U.S. Pat. No. 4,521,422 teaches that the intermediate alkali metal salts of hydroxymethyleneketones (g) can be acylated by reacting with acid chlorides or anhydrides to give O-acyl derivatives (h), and that neutralization of (g) with certain acids affords hydroxymethylene ketones (i), all of which may be reacted with pyrazole (a) to give compounds of structure (I).

Reaction Scheme C

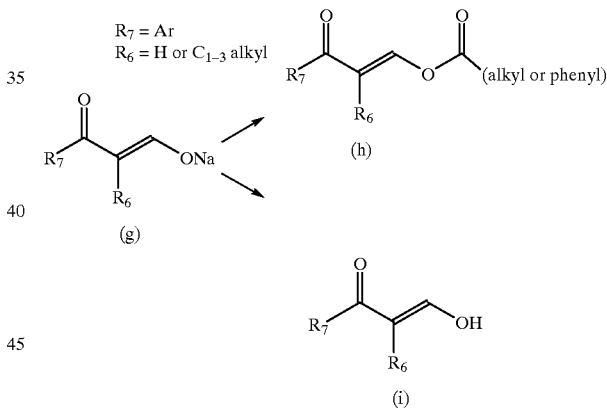

Further, U.S. Pat. No. 4,521,422 discloses that hydroxymethyleneketones (i) may be converted to other aldehyde equivalents, such as alkoxymethyleneketones (j), alkylthiomethyleneketones (k) and aminomethyleneketones (l)—as represented by Reaction Scheme D - and reacted with pyrazole (a) to give compounds of structure (I). Other hydroxymethieneketone and derivatives which are chemical equivalents of the same may also be used, such as 2-(dialkylamino)-1-aryl or (heteroaryl)-2-propen-1-ones.

Reaction Scheme D

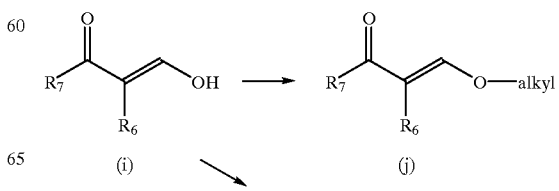

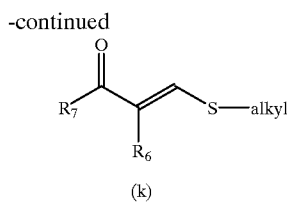

(k)

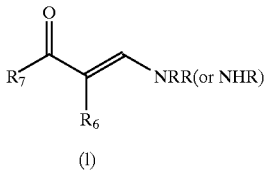

(l)

In addition, other United States patents have issued directed to the synthesis of substituted pyrazolopyrimidines. For example, U.S. Pat. Nos. 4,654,347 and 4,626,538, both to American Cyanamide, disclose substituted pyrazolopyrimidines of structure (I) made by the techniques discussed above, but having different substituents than those of U.S. Pat. No. 4,521,422.

While U.S. Pat. Nos. 4,521,422 and 4,900,836, among others, teach techniques for the synthesis of compounds of structure (I), such procedures are relatively time consuming, involve numerous steps, and are not particularly economical or efficient for large-scale synthesis. Accordingly, there is a need in the art for improved synthetic techniques which overcome these shortcomings. The present invention fulfills these needs, and provides further related advantages.

SUMMARY OF THE INVENTION

In brief, the present invention is directed to the synthesis of substituted pyrazolopyrimidines having the following structure (I), which compounds have utility over a wide range of indications, including treatment of insomnia.

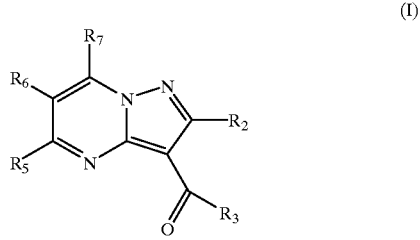

(I)

In structure (I) above, $R_2$, $R_3$, $R_5$, $R_6$ and $R_7$ may be any of a number of substituents, and represent the remainder of the compound. Thus, in one embodiment, the present invention is directed generally to the synthesis of the pyrazolopyrimidine "core" or "template" itself, regardless of the nature of the various R substituents.

In a more specific embodiment, $R_2$, $R_3$, $R_5$, $R_6$ and $R_7$ of structure (I) are as defined in U.S. Pat. No. 4,521,422, but under a different numbering scheme for the respective R groups. In particularly, $R_2$, $R_3$, $R_5$, $R_6$ and $R_7$ of structure (I) correspond to $R_2$, $R_1$, $R_5$, $R_4$ and $R_3$, respectively, of U.S. Pat. No. 4,521,422.

In another more specific embodiment, $R_2$, $R_3$, $R_5$, $R_6$ and $R_7$ of structure (I) are as defined in U.S. Pat. No. 4,654,347, wherein $R_5$ and $R_6$ of structure (I) are both hydrogen and $R_2$, $R_3$ and $R_7$ of structure (I) correspond to $R_2$, $R_1$ and $R_3$, respectively, of U.S. Pat. No. 4,654,347.

In yet another more specific embodiment, $R_2$, $R_3$, $R_5$, $R_6$ and $R_7$ of structure (I) are as defined in U.S. Pat. No. 4,626,538, wherein $R_5$ and $R_6$ of structure (I) are both hydrogen and $R_2$, $R_3$ and $R_7$ of structure (I) correspond to $R_2$, $R_4$ (when $R_1$ is —C(=O)$R_4$) and $R_3$, respectively, of U.S. Pat. No. 4,626,538.

For purpose of convenience, the more specific embodiments disclosed above are also referred to herein as "the R groups of U.S. Pat. Nos. 4,521,422, 4,654,347 and 4,626,538." Thus, in one embodiment, the present invention is directed to the synthesis of substituted pyrazolopyrimidines having structure (I) above, which compounds have utility over a wide range of indications, including treatment of insomnia, wherein structure (I) is substituted with the R groups of U.S. Pat. Nos. 4,521,422, 4,654,347 and 4,626,538.

The synthetic techniques of this invention represent significant improvements over the prior techniques, including those disclosed in U.S. Pat. Nos. 4,521,422 and 4,900,836, particularly with regard to enhanced efficiency for large scale manufacture, reduced cost, better yield and/or simplified reaction conditions. In addition, improved techniques are also disclosed which do not require isolation of the pyrazole intermediate, as well as improved techniques for making intermediates for synthesis of compounds of structure (I).

These and other aspects of this invention will be apparent upon reference to the following detailed description.

DETAILED DESCRIPTION OF THE INVENTION

As mentioned above, the present invention is directed to improved synthetic routes for the synthesis of substituted pyrazolopyrimidines which are active as anxiolytic, anticonvulsant, sedative-hypnotic and skeletal muscle relaxant agents. Such compounds are represented by structure (I) above, and have previously been disclosed in U.S. Pat. Nos. 4,521,422, 4,900,836, 4,654,347 and 4,626,538 (which patents are each incorporated herein by reference in their entirety).

More specifically, in one embodiment of this invention, the pyrazolopyrimidine of structure (I) is N-methyl-N-(3-{3-[2-thienylcarbonyl]-pyrazol-[1,5-α]-pyrimidin-7-yl}phenyl)acetamide, which compound has the following structure (hereinafter referred to as "Compound 1" or "1"):

Compound 1

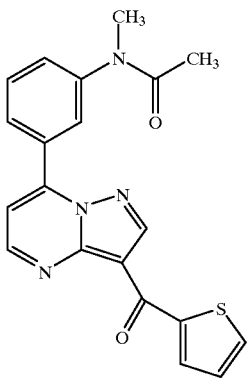

As noted above, U.S. Pat. Nos. 4,521,422 and 4,900,836 disclose the synthesis of compounds of structure (I) via pyrazole intermediate (a). In one embodiment of this invention, synthesis does not proceed by way of this intermediate, which offers significant advantages over prior techniques, including enhanced efficiency, particularly in the context of large scale manufacture.

In one aspect of this embodiment, a compound of structure (I) generally, or Compound 1 specifically, is prepared by the following Reaction Scheme 1.

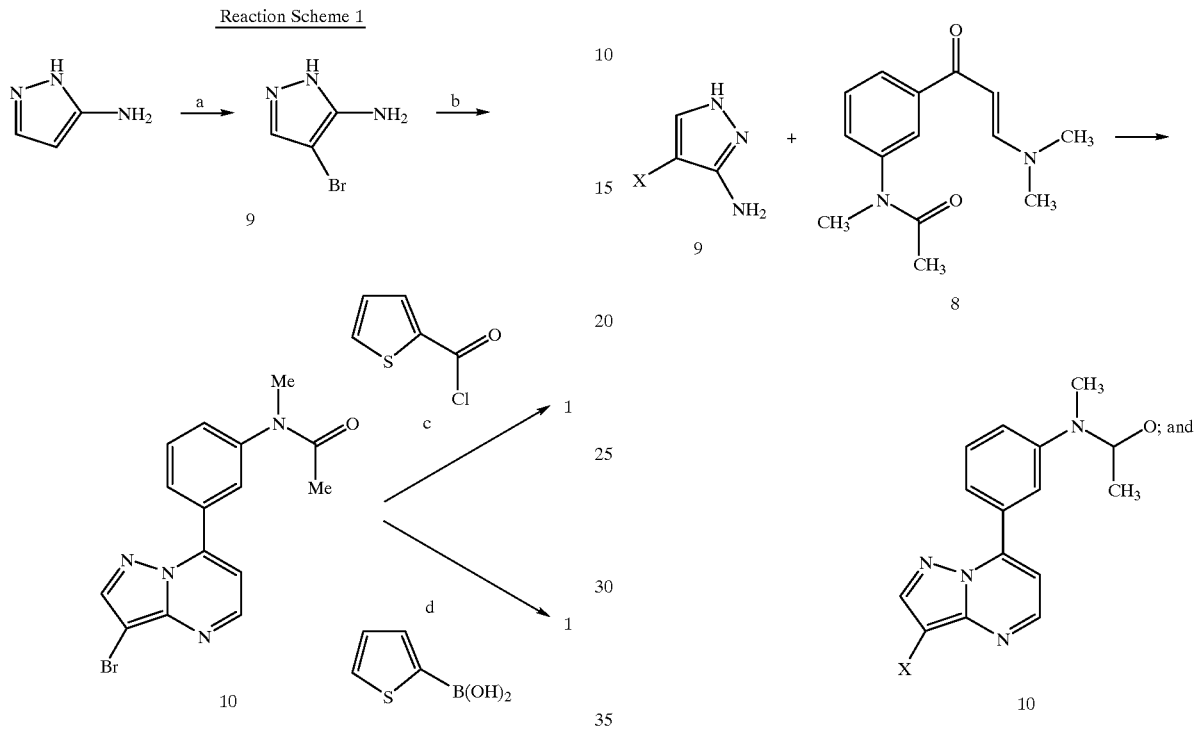

Reagents: (a) Br₂, AcOH; (b) 8, AcOH; (c) Zn or Mg; (d) Pd(0), CO.

wherein compound 8 (see step b above) is an enaminone having the structure:

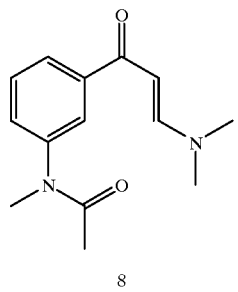

In Reaction Scheme 1, bromination of the aminopyrazole affords the bromopyrazole 9. This is then cyclized with enaminone 8 (which may be made according to the techniques disclosed in U.S. Pat. No. 4,521,422) in acetic acid affording the bromopyrazolopyrimidine 10. This bromopyrazolopyrimidine 10 is then reacted with 2-thiophenecarboxylic acid chloride in the presence of zinc or magnesium affording the desired product, Compound 1. Alternatively, this product may be prepared from the bromopyrazolopyrimidine 10 using a Suzuki coupling with 2-thiophene boronic acid in the presence of carbon monoxide and a palladium catalyst.

Accordingly, in the practice of this aspect of the invention, a method is disclosed for making Compound 1 by the following steps:

(a) reacting pyrazole 9 (X=halogen) with enaminone 8 to yield the corresponding halopyrazolopyrimidine 10

(b) reacting halopyrazolopyrimidine 10 with either (1) 2-thiophenecarboxylic acid chloride in the presence of zinc or magnesium, or (2) 2-thiophene boronic acid in the presence of carbon monoxide and a palladium catalyst, to yield Compound 1.

In another aspect of this embodiment, a compounds of structure (I) generally, or compound I specifically, is prepared as depicted in the following Reaction Scheme 2.

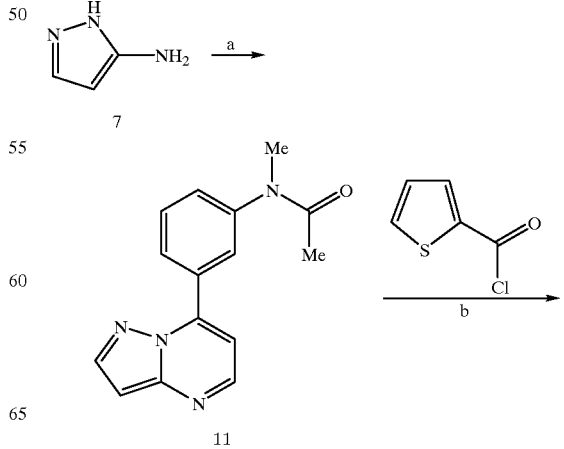

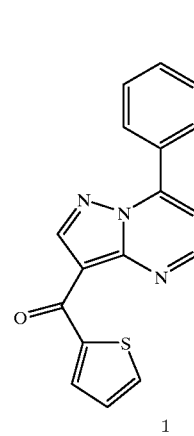

Reagents: (a) 8, AcOH; (b) AlCl₃.

In Reaction Scheme 2, pyrazolopyrimidine 11 prepared by cyclizing aminopyrazole 7 with enaminone 8. This is then reacted under Friedel-Crafts conditions using 2-thiophenecarboxylic acid chloride and an appropriate Lewis acid such as AlCl₃ or ZnCl₂ affording the desired product, Compound 1.

Accordingly, in the practice of this aspect of the invention, a method is disclosed for making Compound 1 by the following steps:

(a) cyclizing aminopyrazole 7 with enaminone 8 to yield pyrazolopyrimidine 11

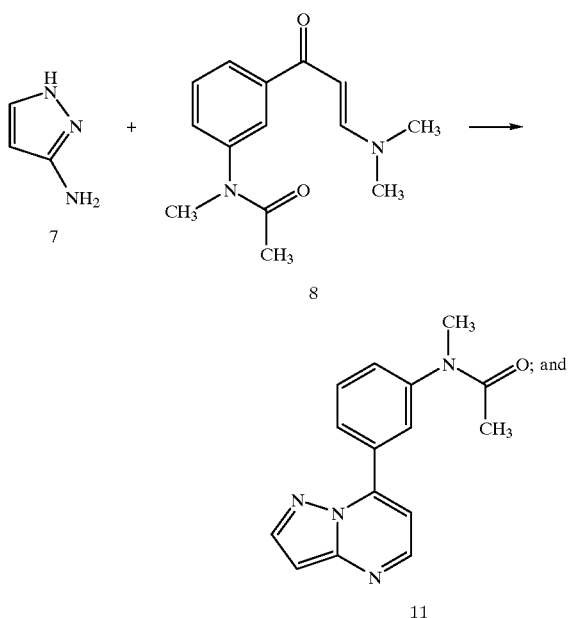

(b) reacting pyrazolopyrimidine 11 with 2-thiophenecarboxylic acid chloride in the presence of a Lewis acid to yield Compound 1.

In a further aspect of this embodiment, a compound of structure (I) generally, or compound 1 specifically, is prepared as depicted in the following Reaction Scheme 3.

Reaction Scheme 3

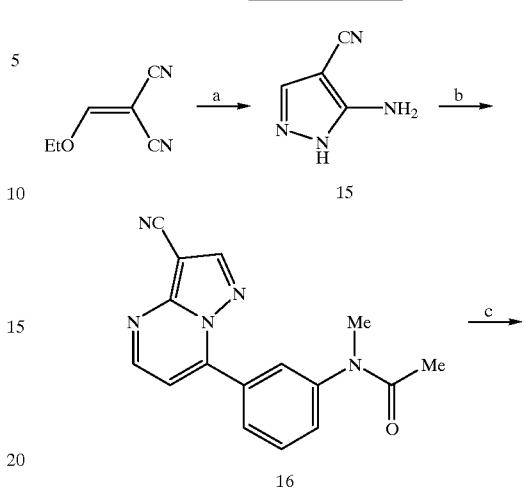

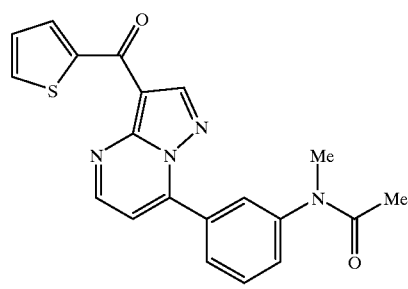

Reagents: (a) hydrazine; (b) 8, AcOH, reflux; (c) 2-bromothiophene, Mg.

In Reaction Scheme 3, preparation of Compound 1 using a Grignard based protocol begins by cyclizing ethoxymethylene malonodinitrile with hydrazine to give the cyanoaminopyrazole 15. Condensation of enamine 8 with 15 in hot acetic acid affords the nitrile intermediate 16. The Grignard reagent is prepared from magnesium and 2-bromothiophene, and reacted with nitrile 16 giving the desired product 1 upon hydrolysis of the intermediate imine. Similarly, addition of 2-lithium thiophene to nitrile 16 also provides the desired product again after hydrolysis of the intermediate imine.

Accordingly, in the practice of this aspect of the invention, a method is disclosed for making Compound 1 by the following steps:

(a) cyclizing cyanoaminopyrazole 15 with enaminone 8 to yield nitrile-pyrazolopyrimidine 16

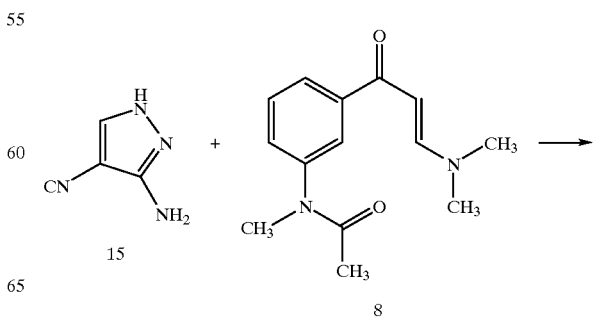

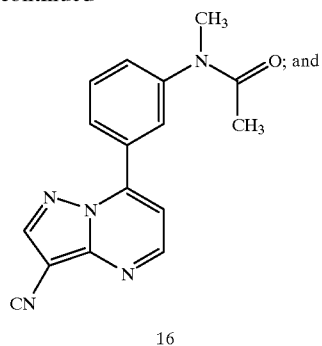

16

(b) reacting nitrile-pyrazolopyrimidine 16 with (1) a Grignard reagent prepared from magnesium and 2-bromothiophene, or (2) with 2-lithium thiophene followed by hydrolysis, to give Compound 1.

In still another aspect of this embodiment, a compound of structure (I) generally, or Compound 1 specifically, is prepared by as depicted in the following Reaction Scheme 4.

In Reaction Scheme 4, coupling of the phenyl amide portion of 1 to the pyrazolopyrimidine begins with aminopyrazole 20. Condensation of 20 with formyl propionic acid methyl ester, or alternatively with ethyl 3,3-diethoxypropionate, affords the pyrazolopyrimidone 21. This is then converted to the chloropyrazolopyrimidine 22 with phosphorus oxychloride using a conventional protocol. Coupling of the boronic acid with 22 using standard Suzuki conditions affords the pyrazolopyrimidine 23. The use of chemistry similar to that disclosed in Reaction Scheme 3 completes the synthesis of 1 (this includes an addition of the Grignard reagent prepared from 2-bromothiophene or the addition of 2-lithiothiophene).

Accordingly, in the practice of this aspect of the invention, a method is disclosed for making Compound 1 by the following steps:

(a) condensation of aminopyrazole 20 with (1) formyl propionic acid methyl ester or (2) ethyl 3,3-diethoxypropionate to yield pyrazolopyrimidone 21

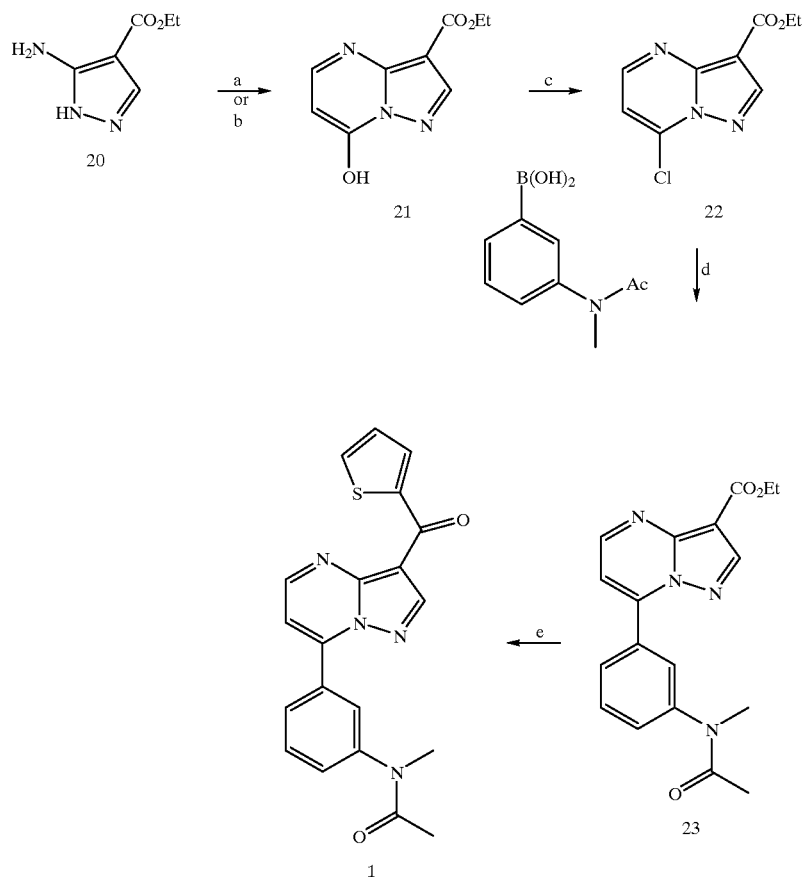

Reaction Scheme 4

Reagents: (a) formylpropionic acid methyl ester, EtOH, Δ; (b) ethyl diethoxypropionate, HOAc, Δ; (c) POCl₃; (d) Pd(Ph₃P)₄, Na₂CO₃, EtOH; (e) 2-bromothiophene, Mg

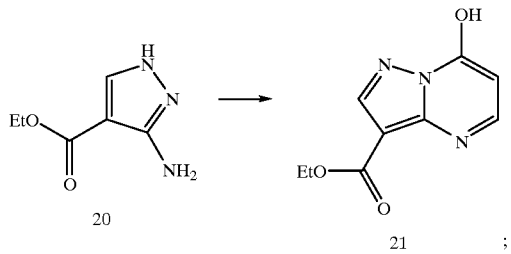

(b) conversion of pyrazolopyrimidone 21 to halopyrazolopyrimidine 22 (where X=halogen)

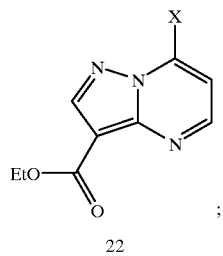

(c) coupling halopyrazolopyrimidine 22 with boronic acid 23 to yield pyrazolopyrimidine 24

(d) reacting pyrazolopyrimidine 24 with (1) a Grignard reagent prepared from magnesium and 2-bromothiophene, or (2) with 2-lithium thiophene followed by hydrolysis, to give Compound 1.

It should be noted that in the above embodiment, synthesis of structure (I) generally, or Compound 1 specifically, does not proceed by way of pyrazole intermediate (a), which offers significant advantages over prior techniques as discussed previously. In another embodiment of this invention, improved techniques are disclosed that do not require isolation of this intermediate, which techniques again also offer significant advantages over existing procedures, including enhance efficiency, particularly in the context of large scale manufacture.

In this embodiment, a compound of structure (I) generally, or Compound 1 specifically, is prepared according to a "one-pot" technique wherein the key steps are conveniently performed without isolation of the pyrazole intermediate (a), as depicted in the following Reaction Scheme 5.

Reaction Scheme 5

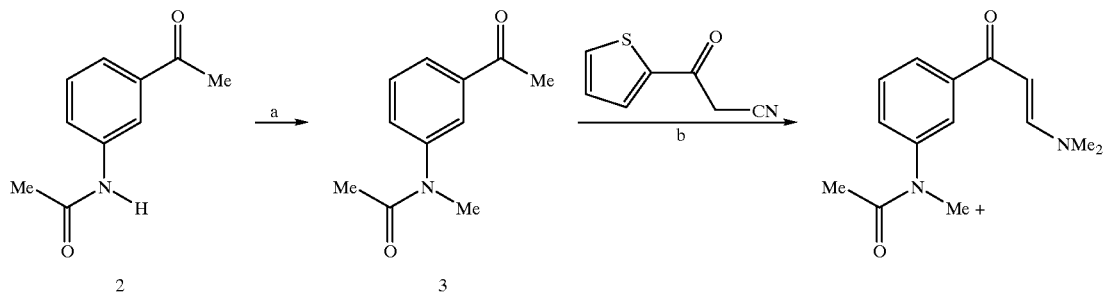

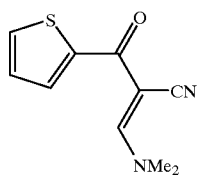

-continued

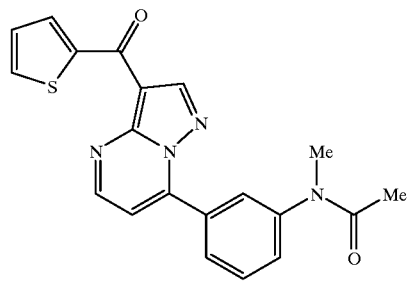

1

Reagents: (a) MeI, NaH, DMF; (b) DMFDMA, toluene; (c) aminoguanidine HNO₃ salt, NaOH, EtOH; (d) AcOH, reflux.

In Reaction Scheme 5, N-alkylation of m-acetamidoacetophenone 2 using conditions of sodium hydride and methyl iodide (or, alternatively, dimethylsulfate) provides acetophenone 3. A mixture of both acetophenone 3 and nitrile 4 are diluted with toluene. An excess of dimethylformamidedimethylacetal (DMFDMA) is added and the mixture refluxed until the starting materials are consumed. A workup involving the removal of toluene and excess DMFDMA is employed to complete this stage of the synthesis. Without isolation of the enaminone intermediates, ethanol is added followed by an appropriate amount of aminoguanidinium nitrate and sodium hydroxide as shown in Reaction Scheme 5. The mixture is heated until consumption of the thiophene intermediate is complete. The crude material is heated in acetic acid and the product is isolated and purified. The benefits of this technique are several, particularly in the context of not having to isolate reaction intermediates, such as the pyrazole intermediate.

(a) alkylating m-acetamidoacetophenone 2 to provide acetophenone 3;

(b) reacting nitrile 4 with acetophenone 3 in the presence of DMFDMA and a solvent until nitrile 4 and acetophenone 3 are consumed;

(c) removing any excess DMFDMA and solvent and, without isolation of the intermediate reaction products from step (b), converting the reaction products upon reaction with aminoguanidine to compound 1; and (d) isolating Compound 1.

In another embodiment, a compound of structure (I) generally, or Compound 1 specifically, is prepared utilizing an improved technique for the synthesis of the pyrazole intermediate, as depicted in the following Reaction Scheme Reaction Scheme 6

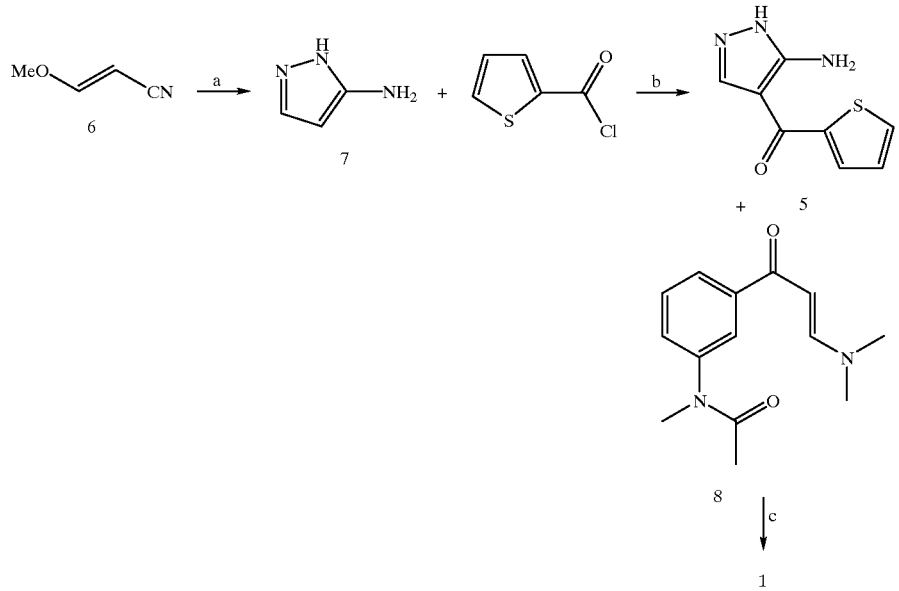

Reagents: (a) NH₂NH₂H₂O; (b) heat; (c) HOAc, reflux

Accordingly, in this embodiment, a method is disclosed for making Compound 1, in a single reaction mixture, by the following steps:

In Reaction Scheme 6, pyrazole 5 is prepared by the treatment of methoxyacrylonitrile 6 with hydrazine to afford the 3-aminopyrazole 7. Addition of 2-thiophenecarboxylic acid chloride to a solution of aminopyrazole 7 initially provides an amide intermediate, which upon heating leads to an intramolecular rearrangement affording pyrazole 5. This is then cyclized with the known enaminone 8 under the standard conditions providing the desired product, Compound 1.

Accordingly, in the practice of this embodiment, a method is disclosed for making Compound 1 by the following steps:

(a) treating methoxyacrylonitrile 6 with hydrazine to afford 3-aminopyrazole 7;

(b) reacting 3-aminopyrazole 7 with 2-thiophenecarboxylic acid chloride to yield pyrazole 5; and (c) cyclizing pyrazole 5 with enaminone 8 to yield Compound 1.

In yet another embodiment, a compound of structure (I) generally, or compound 1 specifically, is prepared by cyclizing the pyrazole intermediate as depicted in the following Reaction Scheme 7.

In still a further embodiment, a compound of structure (I) generally, or Compound 1 specifically, is prepared by cyclizing pyrazole intermediate 5 as depicted in the following Reaction Scheme 8

Reaction Scheme 8

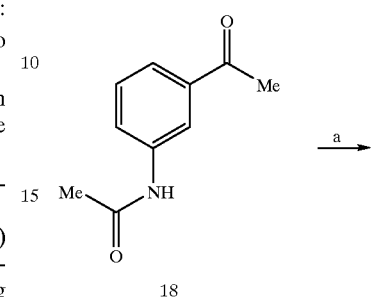

Reaction Scheme 7

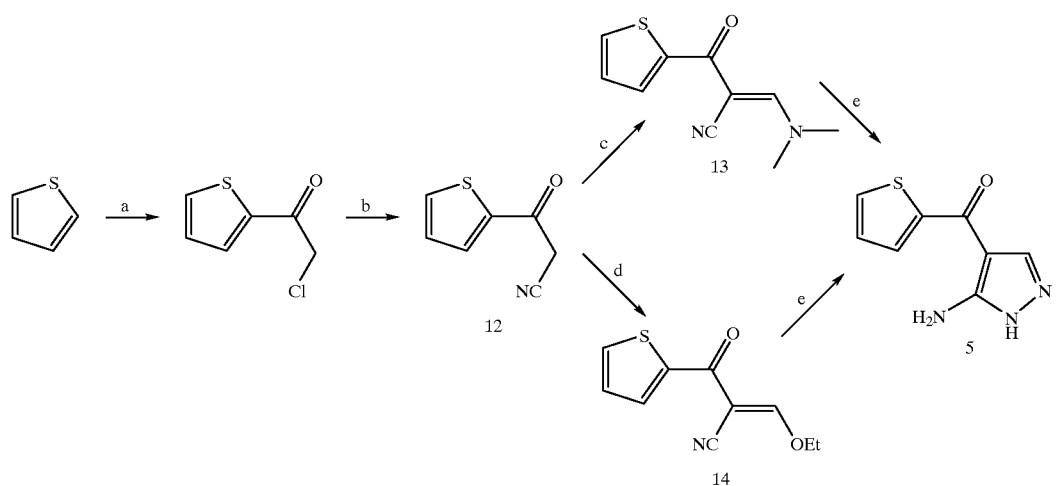

Reagents: (a) AlCl₃; (b) KCN, EtOH; (c) DMFDMA; (d) HC(OEt)₃; (e) aminoguanidine.

In Reaction Scheme 7, thiophene is acylated under Friedel-Crafts conditions with chloroacetylchloride yielding the corresponding acylthiophene. Nucleophilic displacement of the chloride with potassium cyanide affords nitrile 12. This is converted to enaminone 13 with DMFDMA or the ethoxyenolether 14 using triethyl orthoformate. Pyrazole intermediate 5 is prepared from either 13 or 14 using standard conditions involving aminoguanidine or hydrazine.

Accordingly, in the practice of this embodiment, a method is disclosed for making Compound 1 by the following steps:

(a) converting nitrile 12 (which may be obtained by reacting thiophene with chloroacetylchloride to yield 2-thiophenecarboxylic acid chloride, and converting the same to nitrile 12 by displacement of the chloride with cyanide) to (i) enaminone 13 with DMFDMA, or to (ii) ethoxyenolether 14 with triethyl orthoformate; and (c) preparing pyrazole 5 from either enaminone 13 or ethoxyenolether 14; and (d) cyclizing pyrazole 5 with enaminone 8 to yield Compound 1.

-continued

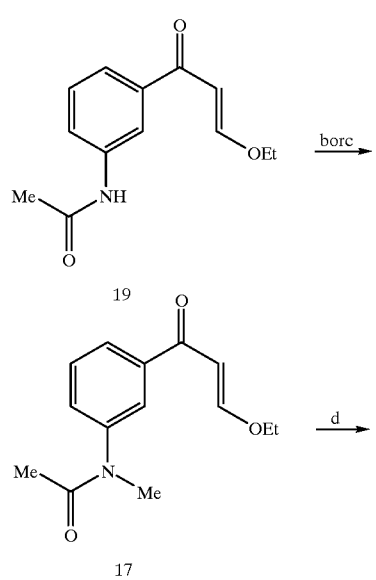

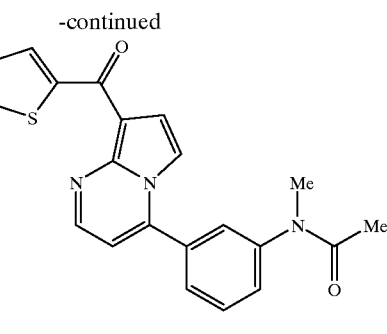

1

Reagents: (a) HC(OEt)₃; (b) MeI, NaH; (c) Me₂SO₄; (d) 5, AcOH, reflux

In Reaction Scheme 8, enol ether 17 is employed in a cyclization reaction. Treatment of the acetophenone 18 with triethyl orthoformate, followed by heating, affords the enol ether 19. This is N alkylated with iodomethane or dimethyl sulfate yielding enol ether 17. Cyclization of 17 with pyrazole intermediate 5 in acetic acid leads to the desired product, Compound 1.

Accordingly, in the practice of this embodiment, a method is disclosed for making Compound I by the following steps:

(a) treatment of acetophenone 18 with triethyl orthoformate to yield enol ether 19;

(b) alkylating enol ether 19 to afford enol ether 17; and (c) cyclizing enol ether 17 with pyrazole 5 to yield Compound 1.

In a preferred embodiment, one or more of the alkylation steps of this invention, particularly the alkylation involved in the formation of enaminone 8 employed in Reaction Schemes 1, 2 and 3 above, occur under phase transfer conditions. As used herein, "phase transfer conditions" means an organic substrate is dissolved in an organic solvent and the nucleophilic reagent is dissolved in an aqueous phase, a phase transfer catalyst is used to carry the nucleophile from the aqueous phase into the organic phase to react with the substrate. More specifically, phase transfer conditions in the context of this invention may be obtained by utilizing, for example, a phase transfer catalyst (such as quaternary ammonium or phosphonium salts, crown ethers and polyethylene glycol ethers) in a polar organic solvent (such as methylene chloride, benzotrifluoride, or toluene) with an aqueous phase containing a base (such as sodium or potassium hydroxide).

Although the above Reaction Schemes 1 through 8 depict the synthesis of Compound 1 specifically, it should be understood that these schemes apply generally to compounds of structure (I) by appropriate selection of the various R groups thereof. Thus, in each of the above Reaction Schemes 1 through 8, the specific R groups associated with the synthesis of Compound 1 may be replaced with the corresponding R groups of U.S. Pat. Nos. 4,521,422, 4,654,347 and 4,626,538 to synthesize the full scope of compounds encompassed within structure (I). Similarly, for each of the intermediates employed in Reaction Schemes 1 through 8, it should be understood that each of these intermediates, while specifically depicted in the context of Compound 1 synthesis, encompass intermediates substituted by the corresponding R groups of U.S. Pat. Nos. 4,521,422, 4,654,347 and 4,626,538.

While the R groups of U.S. Pat. Nos. 4,521,422, 4,654,347 and 4,626,538 are fully disclosed in each of these respective patents, for purpose of completeness they are repeated below (using the number scheme for each of the various R groups as disclosed in those patents):

U.S. Pat. No. 4,521,422:

$R_1$ is selected from the group consisting of unsubstituted phenyl; phenyl mono- or di-substituted by halogen, alkoxy($C_1$–$C_3$) or alkyl($C_1$–$C_3$); phenyl mono-substituted by trifluoromethyl, alkylthio($C_1$–$C_3$), alkylamino($C_1$–$C_3$), dialkylamino($C_1$–$C_3$), methylenedioxy, alkylsulfonyl($CI$-$C_3$) or alkanoylamino($C_1$–$C_3$); naphthalenyl; thiazolyl; biphenyl; thienyl; furanyl; pyridinyl; substituted thiazolyl; substituted biphenyl; substituted thienyl; and substituted pyridinyl wherein the substituents are selected from one or two of the group consisting of halogen, alkoxy($C_1$–$C_3$) and alkyl($C_1$–$C_3$);

$R_2$, $R_4$ and $R_5$ are each selected from the group consisting of hydrogen and alkyl($C_1$–$C_3$); and $R_3$ is selected from the group consisting of unsubstituted phenyl, phenyl mono-substituted by halogen, trifluoromethyl, alkoxy($C_1$–$C_3$), amino, alkyl($C_{1-3}$), alkylamino($C_1$–$C_6$), dialkylamino($C_1$–$C_3$), alkanoylamino($C_1$–$C_6$), N-alkyl($C_1$–$C_6$)alkanoylamino ($C_1$–$C_6$), cyano or alkylthio($C_1$–$C_3$); furanyl; thienyl; pyridinyl; and pyridine-1-oxide.

U.S. Pat. No. 4,654,347:

$R_1$ is selected from the group consisting of unsubstituted phenyl; phenyl mono- or disubstituted by halogen, alkyl($C_1$–$C_3$) or alkoxy($C_1$–$C_3$); phenyl monosubstituted by trifluoromethyl, alkylthio($C_1$–$C_3$), alkylamino ($C_1$–$C_3$), dialkylamino($C_1$–$C_3$), methylenedioxy, alkylsulfonyl($C_1$–$C_3$) or alkanoylamino($C_1$–$C_3$); naphthalenyl; thiazolyl; biphenyl; thienyl; furanyl; pyridinyl; substituted thiazolyl; substituted biphenyl; substituted thienyl; and substituted pyridinyl, wherein the substituents are selected from one or two of the groups consisting of halogen, alkyl($C_1$–$C_3$) and alkoxy ($C_1$–$C_3$);

$R_2$ is selected from the group consisting of hydrogen and alkyl($C_1$–$C_3$);

$R_3$ is

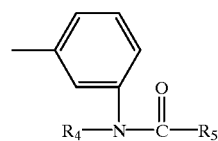

$R_4$ is selected from the group consisting of hydrogen, alkenyl($C_2$–$C_6$), —$CH_2C\equiv CH$, cycloalkyl($C_3$–$C_6$) methyl, —$CH_2OCH_3$ and —$CH_2CH_2OCH_3$; and $R_5$ is selected from the group consisting of hydrogen, cycloalkyl($C_{3-6}$), —O-alkyl($C_1$–$C_6$), —NH-alkyl ($C_1$–$C_3$), —N-dialkyl($C_1$–$C_3$), —($CH_2$)$_n$—alkyl ($C_1$–$C_3$), —($CH_2$)$_n$—NH-alkyl($C_1$–$C_3$), —($CH_2$)$_n$— N-dialkyl($C_1$–$C_3$), where n is an integer 1 to 3 inclusive, and $R_5$ may be alkyl($C_1$–$C_6$), when $R_4$ is not hydrogen.

U.S. Pat. No. 4,626.538:

$R_1$ is —$C(=O)R_4$;

$R_2$ is selected from the group consisting of hydrogen and alkyl($C_1$–$C_3$);

R$_3$ is

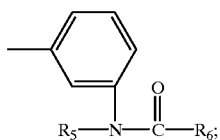

R$_4$ is selected from the group consisting of hydrogen, alkyl(C$_1$-C$_6$) and alkoxy(C$_1$-C$_6$);

R$_5$ is selected from the group consisting of hydrogen, alkyl(C$_1$-C$_6$), alkenyl(C$_2$-C$_6$), —CH$_2$C≡CH, cycloalkyl(C$_3$-C$_6$)methyl, —CH$_2$OCH$_3$ and —CH$_2$CH$_2$OCH$_3$; and R$_6$ is selected from the group consisting of alkyl (C$_1$-C$_6$), cycloalkyl(C$_3$-C$_6$), —O alkyl(C$_1$-C$_6$), —NH-alkyl(C$_1$-C$_3$), —N-dialkyl(C$_1$-C$_3$), (CH$_2$)$_n$—O-alkyl(C$_1$-C$_3$), —(CH$_2$)$_n$—NH-alkyl(C$_1$-C$_3$) and —(CH$_2$)n—N-dialkyl(C$_1$-C$_3$), where n is an integer 1 to 3 inclusive.

In addition to the above synthetic embodiments, the present invention is also directed to substituted pyrazolopyrimidines of structure (I), particularly Compound 1, made according to any one (or more) of the methods of this invention, as well as to novel intermediates therefor, including each of the intermediates set forth in Reaction Schemes 1 through 8 above with appropriate substitution by the corresponding R groups of U.S. Pat. Nos. 4,521,422, 4,654,347 and 4,626,538.

The substituted pyrazolopyrimidines of this invention have utility as anxiolytic, anticonvulsant, sedative-hypnotic and skeletal muscle relaxant agents. More specifically, these compounds have particular utility in the context of treating insomnia by inducing sedation or hypnosis, as well as skeletal muscle relaxation. Typically, such compounds are administered in the form of a pharmaceutical composition, in dosage unit form, in an amount which is effective to treat the condition of interest comprising. Generally, this is from about 1–750 mg of compound in combination with an appropriate pharmaceutically acceptable carrier. In a typical embodiment, the compound is present in the pharmaceutical composition in an amount ranging from 2 mg to 60 mg per dosage depending upon the route of administration. Appropriate concentrations and dosages can be readily determined by one skilled in the art.

Pharmaceutically acceptable carriers are familiar to those skilled in the art. For compositions formulated as liquid solutions, acceptable carriers include saline and sterile water, and may optionally include antioxidants, buffers, bacteriostats and other common additives. The compositions can also be formulated as pills, capsules, granules, or tablets which contain, in addition to a compound of structure (I), diluents, dispersing and surface active agents, binders, and lubricants. One skilled in this art may further formulate the compound in an appropriate manner, and in accordance with accepted practices, such as those disclosed in *Remington's Pharmaceutical Sciences*, Gennaro, Ed., Mack Publishing Co., Easton, Pa. 1990.

As noted above, the compounds of this invention have utility in the context of treating conditions which benefit from administration of agents which possess anxiolytic, anti-anoxic, sleep-inducing, hypnotic, anticonvulsant, and/or skeletal muscle relaxant properties. Such conditions include insomnia specifically, as well as sleep disorders generally and other neurological and psychiatric complaints, anxiety states, vigilance disorders, such as for combating behavioral disorders attributable to cerebral vascular damage and to the cerebral sclerosis encountered in geriatrics, epileptic vertigo attributable to cranial trauma, and for metabolic encephalopathies.

Representative routes of administration to a patient in need thereof include systemic administration, preferably in the form of a pharmaceutical composition as noted above. As used herein, systemic administration encompasses both oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parenteral administration, the compounds of the present invention can be prepared in aqueous injection solutions which may contain buffers, antioxidants, bacteriostats, and other additives commonly employed in such solutions.

The following example is offered by way of illustration, not limitation.

EXAMPLE

Formation of Enaminone 8 of Reaction Schemes 1, 2 and/or 3 Under Phase Transfer Conditions

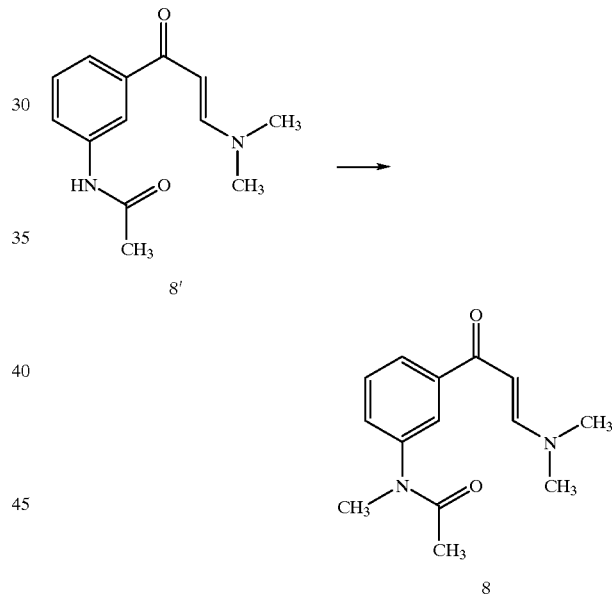

To enaminone 8' (25 g, 107.6 mmol) in benzotrifluoride (92 mL) and dichloromethane (160 mL) was added tetrabutylammonium sulfate (2 g, 5.9 mmol). To the mixture was added of dimethyl sulfate (16 g, 126.7 mmol). To the mixture was added 200 g of 50% aqueous sodium hydroxide solution and the mixture vigorously stirred for 6 hours, keeping the reaction temperature less than 40° C. Upon consumption of starting material, 200 mL of water was carefully added keeping the reaction temperature less than 40° C. The aqueous phase was separated and the organic phase was washed three times with water and dried over magnesium sulfate. The dichloromethane was removed in vacuo affording a yellow solid. The solid was filtered, washed with benzotrifluoride and dried in vacuo affording alkylated enaminone 8 (19 g, 72% yield).

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. A method for making N-methyl-N-(3-{3-[2-thienylcarbonyl]-pyrazol-[1,5-α]-pyrimidin-7-yl}phenyl) acetamide (Compound 1), comprising the following steps:

(a) reacting pyrazole 9 with enaminone 8 to yield the corresponding halopyrazolopyrimidine 10, wherein X is hydrogen

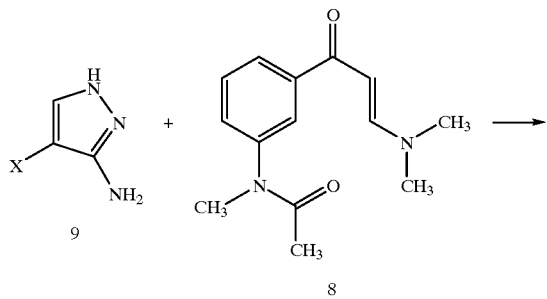

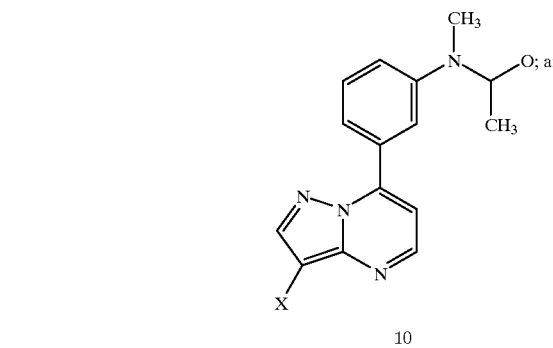

(b) reacting halopyrazolopyrimidine 10 with either (1) 2-thiophenecarboxylic acid chloride in the presence of zinc or magnesium, or (2) 2-thiophene boronic acid in the presence of carbon monoxide and a palladium catalyst, to yield Compound 1.

2. A method for making N-methyl-N-(3-{3-[2-thienylcarbonyl]-pyrazol-[1,5-α]-pyrimidin-7-yl}phenyl) acetamide (Compound 1), comprising the following steps:

(a) cyclizing aminopyrazole 7 with enaminone 8 to yield pyrazolopyrimidine 11

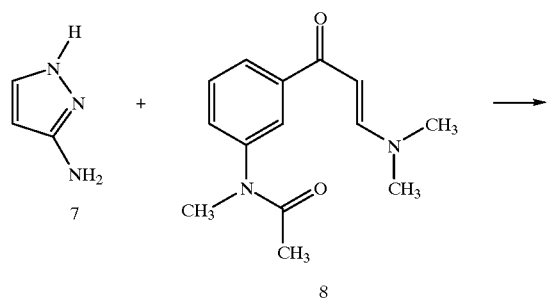

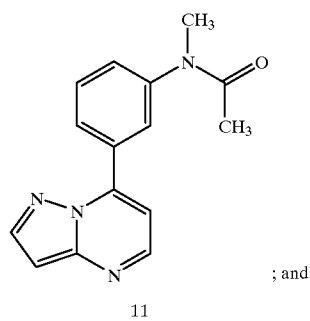

(b) reacting pyrazolopyrimidine 11 with 2-thiophenecarboxylic acid chloride in the presence of a Lewis acid to yield Compound 1.

3. A method for making N-methyl-N-(3-{3-[2-thienylcarbonyl]-pyrazol-[1,5-α]-pyrimidin-7-yl}phenyl) acetamide (Compound 1), comprising the following steps:

(a) cyclizing cyanoaminopyrazole 15 with enaminone 8 to yield nitrile-pyrazolopyrimidine 16

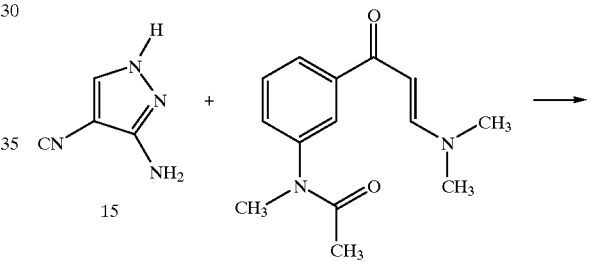

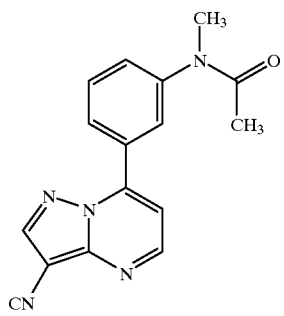

(b) reacting nitrile-pyrazolopyrimidine 16 with (1) a Grignard reagent prepared from magnesium and 2-bromothiophene, or (2) with 2-lithium thiophene followed by hydrolysis, to give compound 1.

4. The method of any one of claim 1, 2 or 3 wherein enaminone 8 is made from enaminone 8' by an alkylation step under phase transfer conditions

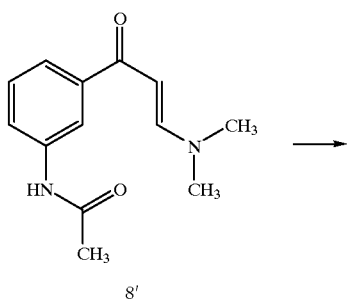

8'

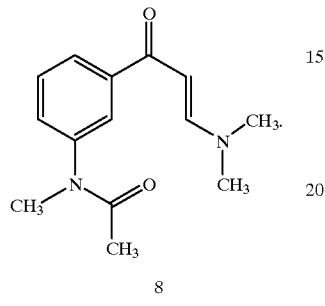

8

5. The method of claim 4 wherein the phase transfer conditions comprise a phase transfer catalyst in a polar organic solvent with an aqueous phase containing a base.

6. The method of claim 5 wherein the phase transfer catalyst is a quaternary ammonium or phosphonium salt, a crown ether or a polyethylene glycol ether.

7. The method of claim 5 wherein the organic solvent is methylene chloride, benzotrifluoride or toluene.

8. The method of claim 5 wherein the base of the aqueous phase is sodium or potassium hydroxide.

9. A method for making N-methyl-N-(3-{3-[2-thienylcarbonyl]-pyrazol-[1,5-α]-pyrimidin-7-yl}phenyl)acetamide (Compound 1), comprising the following steps:

(a) treating acetophenone 18 with triethyl orthoformate to yield enol ether

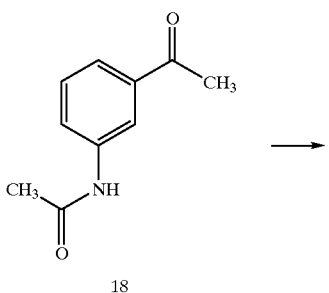

18

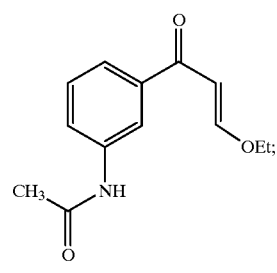

19

(b) alkylating enol ether 19 to afford enol ether 17

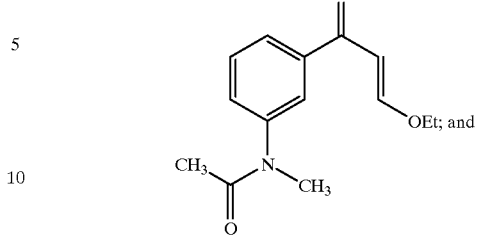

17

(c) cyclizing enol ether 17 with pyrazole 5 to yield Compound 1

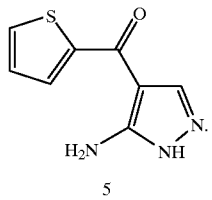

5

10. A method for making alkylated enaminone 8, comprising the step of alkylating enaminone 8' under phase transfer conditions

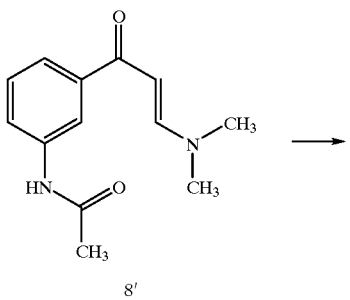

8'

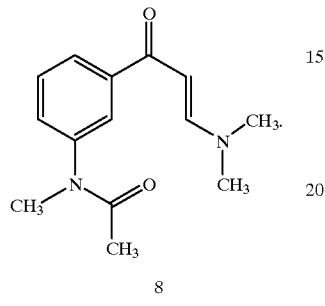

8

11. The method of claim 10 wherein the phase transfer conditions comprise a phase transfer catalyst in a polar organic solvent with an aqueous phase containing a base.

12. The method of claim 11 wherein the phase transfer catalyst is a quaternary ammonium or phosphonium salt, a crown ether or a polyethylene glycol ether.

13. The method of claim 11 wherein the organic solvent is methylene chloride, benzotrifluoride or toluene.

14. The method of claim 11 wherein the base of the aqueous phase is sodium or potassium hydroxide.

15. The method of claim 10, further comprising the step of utilizing enaminone 8 as an intermediate in the synthesis of N-methyl-N-(3-{3-[2-thienylcarbonyl]-pyrazol-[1,5-α]-pyrimidin-7-yl}phenyl)acetamide (Compound 1).

16. The method of claim 15 wherein the step of utilizing enaminone 8 as an intermediate comprises reacting enaminone 8 with a pyrazole to form Compound 1.

17. The method of claim 16 wherein the pyrazole has the structure:

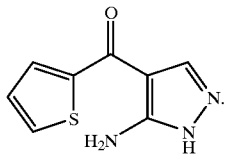

18. A method for making N-methyl-N-(3-{3-[2-thienylcarbonyl]-pyrazol-[1,5-α]-pyrimidin-7-yl}phenyl)acetamide (Compound 1), comprising the following steps:
   (a) condensing aminopyrazole 20 with (1) formyl propionic acid methyl ester, or (2) ethyl 3,3-diethoxypropionate, to yield pyrazolopyrimidone 21

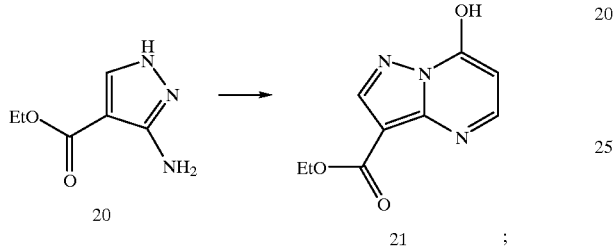

(b) converting pyrazolopyrimidone 21 to halopyrazolopyrimidine 22, wherein X is halogen

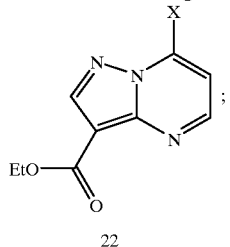

(c) coupling halopyrazolopyrimidine 22 with boronic acid 23 to yield pyrazolopyrimidine 24

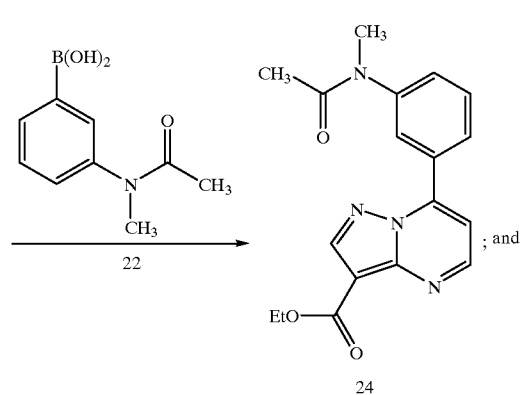

(d) reacting pyrazolopyrimidine 24 with (1) a Grignard reagent prepared from magnesium and 2-bromothiophene, or (2) with 2-lithium thiophene followed by hydrolysis, to give Compound 1.

19. A method for making N-methyl-N-(3-{3-[2-thienylcarbonyl]-pyrazol-[1,5-α]-pyrimidin-7-yl}phenyl)acetamide (Compound 1), comprising the following steps:

(a) alkylating m-acetamidoacetophenone 2 to provide acetophenone 3

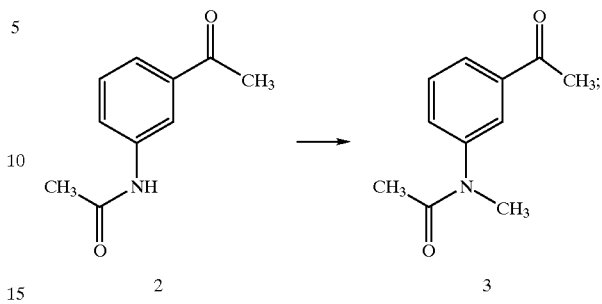

(b) reacting nitrile 4 with acetophenone 3 in the presence of dimethylformamidedimethylacetal (DMFDMA) and a solvent until nitrile 4 and acetophenone 3 are consumed

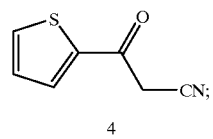

(c) removing any excess DMFDMA and solvent and, without isolation of the intermediate reaction products from step (b), converting the reaction products upon reaction with aminoguanidine to Compound 1; and (d) isolating Compound 1.

20. A method for making N-methyl-N(3-{3-[2-thienylcarbonyl]-pyrazol-[1,5-α]-pyrimidin-7-yl}phenyl)acetamide (Compound 1), comprising the following steps:

(a) treating methoxyacrylonitrile 6 with hydrazine to afford 3-aminopyrazole 7;

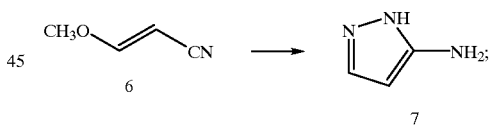

(b) reacting 3-aminopyrazole 7 with 2-thiophenecarboxylic acid chloride to yield pyrazole 5

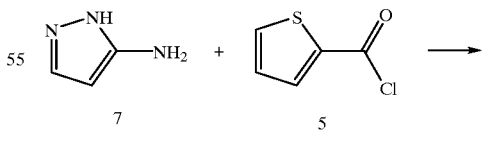

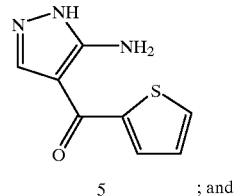

(c) cyclizing pyrazole 5 with enaminone 8 to yield Compound 1

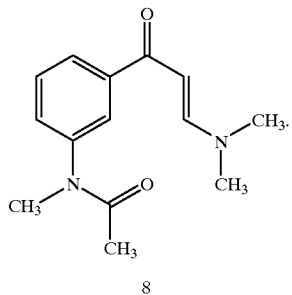

8

21. A method for making N-methyl-N-(3-{3-[2-thienylcarbonyl]-pyrazol-[1,5-α]-pyrimidin-7-yl}phenyl)acetamide (Compound 1), comprising the following steps:

(a) converting nitrile 12 to (i) enaminone 13 with dimethylformamidedimethylacetal (DMFDMA), or to (ii) ethoxyenolether 14 with triethyl orthoformate

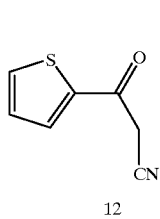

12

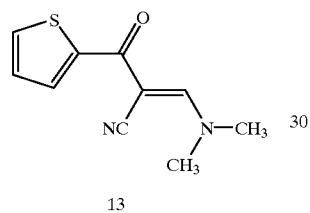

13

-continued

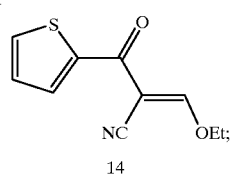

14

(b) preparing pyrazole 5 from either enaminone 13 or ethoxyenolether 14

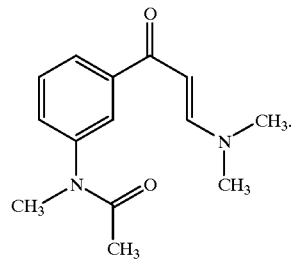

5

(c) cyclizing pyrazole 5 with enaminone 8 to yield compound 1

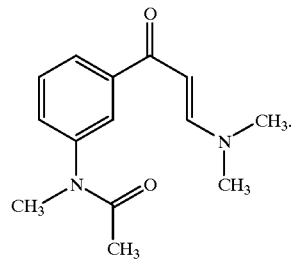

8

* * * * *

UNITED STATES PATENT AND TRADEMARK OFFICE
CERTIFICATE OF CORRECTION

PATENT NO. : 6,472,528 B1
DATED : October 29, 2002
INVENTOR(S) : Raymond S. Gross et al.

It is certified that error appears in the above-identified patent and that said Letters Patent is hereby corrected as shown below:

Title page,
Item [75], Inventors, should read as: -- Raymond S. Gross, Poway, CA (US); Keith M. Wilcoxen, San Diego, CA (US); Richard Oglesby, Schodack Landing, NY (US) --.
Item [57], ABSTRACT,
Lines 2-4, should read as -- N-methyl-N-(3-{3-[2-thienylcarbonyl]-pyrazol-[1,5-α]-pyrimidin-7-yl}phenyl)acetamide. --.

Column 21,
Lines 11 and 12, "wherein X is hydrogen" should read as -- wherein X is halogen --.

Signed and Sealed this

Third Day of June, 2003

JAMES E. ROGAN
*Director of the United States Patent and Trademark Office*